(12) United States Patent
Rao et al.

(10) Patent No.: US 11,054,315 B2
(45) Date of Patent: Jul. 6, 2021

(54) THERMALLY ISOLATED THERMOCOUPLE

(71) Applicant: Biosense Webster (Israel) Ltd., Yokneam (IL)

(72) Inventors: Anand Rao, Tustin, CA (US); Thomas Selkee, Claremont, CA (US); Keshava Datta, Chino Hills, CA (US); Thanh Nguyen, El Monte, CA (US)

(73) Assignee: Biosense Webster (Israel) Ltd., Yokneam (IL)

(*) Notice: Subject to any disclaimer, the term of this patent is extended or adjusted under 35 U.S.C. 154(b) by 259 days.

(21) Appl. No.: 15/867,451

(22) Filed: Jan. 10, 2018

(65) Prior Publication Data
US 2019/0212207 A1 Jul. 11, 2019

(51) Int. Cl.
| | | |
|---|---|---|
| *G01K 7/00* | (2006.01) | |
| *G01K 1/00* | (2006.01) | |
| *G01K 7/06* | (2006.01) | |
| *A61B 18/14* | (2006.01) | |
| *G01K 7/02* | (2021.01) | |
| *G01K 1/12* | (2006.01) | |
| *G01K 7/10* | (2006.01) | |
| *G01K 13/02* | (2021.01) | |
| *A61B 18/00* | (2006.01) | |

(52) U.S. Cl.
CPC ............ *G01K 7/06* (2013.01); *A61B 18/1492* (2013.01); *G01K 1/125* (2013.01); *G01K 7/02* (2013.01); *G01K 7/10* (2013.01); *G01K 13/02* (2013.01); *A61B 2018/00029* (2013.01); *A61B 2018/00577* (2013.01); *A61B 2018/00797* (2013.01); *A61B 2018/00821* (2013.01)

(58) Field of Classification Search
USPC ................. 374/179, 208, 166, 110; 600/549
See application file for complete search history.

(56) References Cited

U.S. PATENT DOCUMENTS

| | | | | |
|---|---|---|---|---|
| 2,012,465 | A | | 8/1935 | Godecke |
| 3,716,417 | A | | 2/1973 | Evans |
| 4,028,139 | A | * | 6/1977 | Smith ........................ B01J 8/02 136/230 |
| 4,385,197 | A | * | 5/1983 | Schwagerman ......... G01K 7/04 136/221 |
| 4,410,756 | A | * | 10/1983 | Schwagerman ......... G01K 1/14 136/201 |
| 5,137,582 | A | | 8/1992 | Kasman |

(Continued)

FOREIGN PATENT DOCUMENTS

WO         96/05768      2/1996

OTHER PUBLICATIONS

European Search Report and Opinion for European Patent Application No. 19150938.9; dated May 10, 2019.

*Primary Examiner* — Mirellys Jagan
(74) *Attorney, Agent, or Firm* — Dergosits & Noah LLP; Todd A. Noah

(57) ABSTRACT

A thermocouple assembly may feature a plurality of temperature sensors formed by thermocouple junctions. The sensors may be disposed within an inner diameter of the tubular element and sealed within the tubular element by thermally conductive material. An air gap may be defined by the thermally conductive material and the interior diameter of the tubular element between each pair of adjacent temperature sensors to improve thermal isolation.

14 Claims, 4 Drawing Sheets

(56) References Cited

U.S. PATENT DOCUMENTS

| | | | |
|---|---|---|---|
| 5,391,199 A | | 2/1995 | Ben-Haim |
| 6,162,184 A | * | 12/2000 | Swanson ................. A61B 18/00 |
| | | | 600/549 |
| 6,197,021 B1 | * | 3/2001 | Panescu ............... A61B 5/0422 |
| | | | 374/E1.005 |
| 6,239,724 B1 | | 5/2001 | Doron et al. |
| 6,332,089 B1 | | 12/2001 | Acker et al. |
| 6,468,260 B1 | | 10/2002 | Bumbalough et al. |
| 6,484,118 B1 | | 11/2002 | Govari |
| 6,500,167 B1 | | 12/2002 | Webster, Jr. |
| 6,522,933 B2 | | 2/2003 | Nguyen |
| 6,618,612 B1 | | 9/2003 | Acker et al. |
| 6,690,963 B2 | | 2/2004 | Ben-Haim et al. |
| 7,729,742 B2 | | 6/2010 | Govari |
| 8,437,832 B2 | | 5/2013 | Govari et al. |
| 8,617,087 B2 | | 12/2013 | Schultz |
| 9,675,411 B2 | | 6/2017 | Govari et al. |
| 2004/0068178 A1 | | 4/2004 | Govari |
| 2011/0013669 A1 | * | 1/2011 | Raj ........................ G01K 7/02 |
| | | | 374/179 |
| 2011/0130648 A1 | | 6/2011 | Beeckler et al. |
| 2013/0261620 A1 | * | 10/2013 | Brannan ................ A61B 5/01 |
| | | | 606/41 |
| 2014/0171821 A1 | * | 6/2014 | Govari .................... A61B 5/01 |
| | | | 600/549 |
| 2015/0342671 A1 | * | 12/2015 | Govari .................... A61B 5/01 |
| | | | 600/549 |
| 2016/0278856 A1 | | 9/2016 | Panescu et al. |
| 2016/0287326 A1 | | 10/2016 | Tegg et al. |
| 2019/0117298 A1 | * | 4/2019 | Beeckler ............. A61B 18/082 |

\* cited by examiner

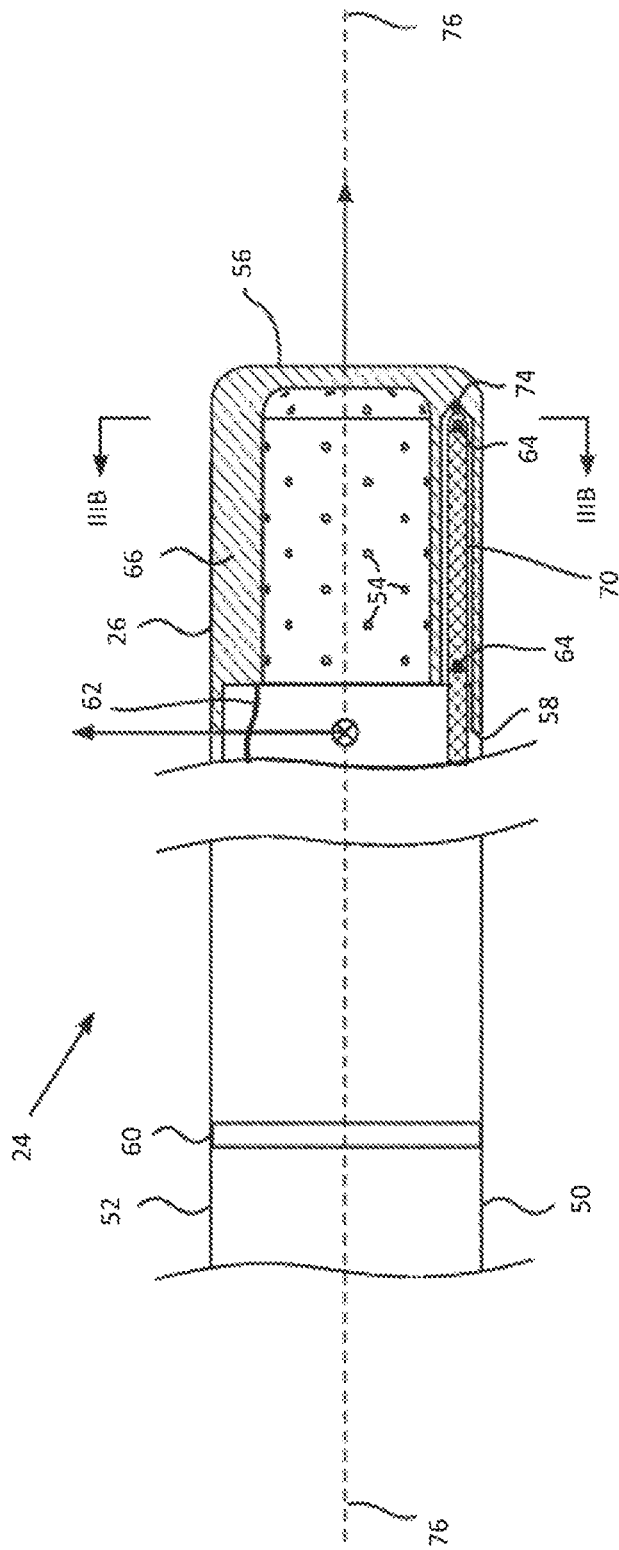
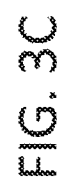
FIG. 3A
FIG. 3B
FIG. 3C

THERMALLY ISOLATED THERMOCOUPLE

FIELD OF THE PRESENT DISCLOSURE

This disclosure relates generally to methods and devices for percutaneous medical treatment, and specifically to catheters that have temperature sensing capabilities, such as ablation catheters. More particularly, this disclosure relates to a thermocouple assembly for use in such catheters that allow more accurate temperature sensing at multiple locations.

BACKGROUND

Radiofrequency (RF) electrode catheters have been in common use in medical practice for many years. They are used to stimulate and map electrical activity in the heart and to ablate sites of aberrant electrical activity. Specifically, targeted ablation may be performed for a number of indications. For example, ablation of myocardial tissue is well known as a treatment for cardiac arrhythmias by using a catheter to apply RF energy and create a lesion to break arrhythmogenic current paths in the cardiac tissue. As another example, a renal ablation procedure may involve the insertion of a catheter having an electrode at its distal end into a renal artery in order to complete a circumferential lesion in the artery in order to denervate the artery for the treatment of hypertension.

In such procedures, a reference electrode is typically provided and may be attached to the skin of the patient or by means of a second catheter. RF current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the target tissue resulting in formation of a lesion which is electrically non-conductive. The lesion may be formed in tissue contacting the electrode or in adjacent tissue. During this process, heating of the electrode also occurs as a result of conduction from the heated tissue to the electrode itself.

As will be appreciated, it is desirable to employ catheters that can sense temperature to help guide the procedure, such as by offering an indication when an efficient ablation temperature has been reached or by reducing conditions under which tissue may be overheated. When the electrode reaches critical temperatures, denaturation of blood proteins causes coagulum formation. Impedance can then rise and limit current delivery. Within tissue, overheating can cause steam bubble formation (steam "pops") with risk of uncontrolled tissue destruction or undesirable perforation of bodily structures. Although ablation catheters may be irrigated to provide greater control over the temperature of catheter components and the surrounding tissue, it is still important to accurately monitor temperature at multiple locations. Indeed, the flow of irrigation fluid may be tailored in part based on feedback from the temperature sensors. For example, Biosense Webster Inc. (Diamond Bar, Calif.) offers the ThermoCool® irrigated-tip catheter for use with its CARTO® integrated mapping and ablation system. The metal catheter tip, which is energized with radio-frequency (RF) electrical current to ablate the tissue, has a number of peripheral holes, distributed circumferentially around the tip, for irrigation of the treatment site. A pump coupled to the catheter delivers saline solution to the catheter tip, and the solution flows out through the holes during the procedure in order to cool the catheter tip and the tissue. Representative details concerning irrigated ablation catheters may be found in commonly-owned U.S. Pat. No. 9,675,411, whose disclosure is incorporated herein by reference in its entirety.

While ablation catheters have been discussed as being a representative example, one of ordinary skill in the art will recognize that many types of intravascular devices may benefit from improved temperature sensing capabilities. Accordingly, it would be desirable to provide a thermocouple assembly design that may used with an ablation catheter or other intravascular device that allows sensing of temperature at multiple locations. Further, it would be desirable to enhance the thermal isolation between the multiple locations to provide more accurate temperature measurement. As will be described in the following materials, this disclosure satisfies these and other needs.

SUMMARY

The present disclosure is directed to a thermocouple assembly for use with an electrode, comprising a plurality of temperature sensors formed by thermocouple junctions, a tubular element, wherein the plurality of temperature sensors are disposed within an inner diameter of the tubular element, a thermally conductive material sealing each of the plurality of temperature sensors within the tubular element and an air gap defined by the thermally conductive material and the interior diameter of the tubular element between each pair of adjacent temperature sensors.

In one aspect, the plurality of temperature sensors may include a proximal sensor and a distal sensor. At least one additional temperature sensor may be positioned between the proximal sensor and the distal sensor.

In one aspect, the thermally conductive material may electrically insulate each of the plurality of temperature sensors.

In one aspect, the tubular element may be at least one of quartz, glass and polyimide.

In one aspect, the thermally conductive material comprises an epoxy. The epoxy may have a filler that increases thermal conductivity in the range of approximately 40-80% by weight.

In one aspect, the thermally conductive material may be a UV curing adhesive.

In one aspect, the thermally conductive material may have a thermal conductivity of at least 3.5 W/m*K.

In one aspect, leads connecting to the plurality of sensors may be twisted to axially constrain the plurality of temperature sensors.

In one aspect, the thermocouple assembly may be secured to an electrode. The thermocouple assembly may be disposed within a longitudinal bore of the electrode. The thermocouple assembly and the longitudinal bore of the electrode may have a nominal clearance of less than approximately 0.002 inches.

This disclosure is also directed to a method for forming a thermocouple assembly. The method may include creating a plurality of temperature sensors with thermocouple junctions, disposing the plurality of temperature sensors within an inner diameter of the tubular element, sealing each of the plurality of temperature sensors within the tubular element with a thermally conductive material and defining an air gap between each pair of adjacent temperature sensors with the thermally conductive material and the interior diameter of the tubular element.

In one aspect, sealing each of the plurality of the temperature sensors within the tubular element may electrically insulate each of the plurality of temperature sensors.

In one aspect, leads connecting to the plurality of temperature sensors may be twisted to axially constrain the plurality of temperature sensors.

In one aspect, the thermocouple assembly may be secured to an electrode. Securing the thermocouple assembly to the electrode may include disposing the thermocouple assembly within a longitudinal bore of the electrode.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIGS. 3A, 3B and 3C schematically illustrate a distal end of the catheter of FIG. 1 showing a tip shell electrode with thermocouples in accordance with an embodiment of the present invention.

DETAILED DESCRIPTION

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner Unless defined otherwise, all technical and scientific terms used herein have the same meaning as commonly understood by one having ordinary skill in the art to which the disclosure pertains.

Finally, as used in this specification and the appended claims, the singular forms "a", "an" and "the" include plural referents unless the content clearly dictates otherwise.

Figure 1:
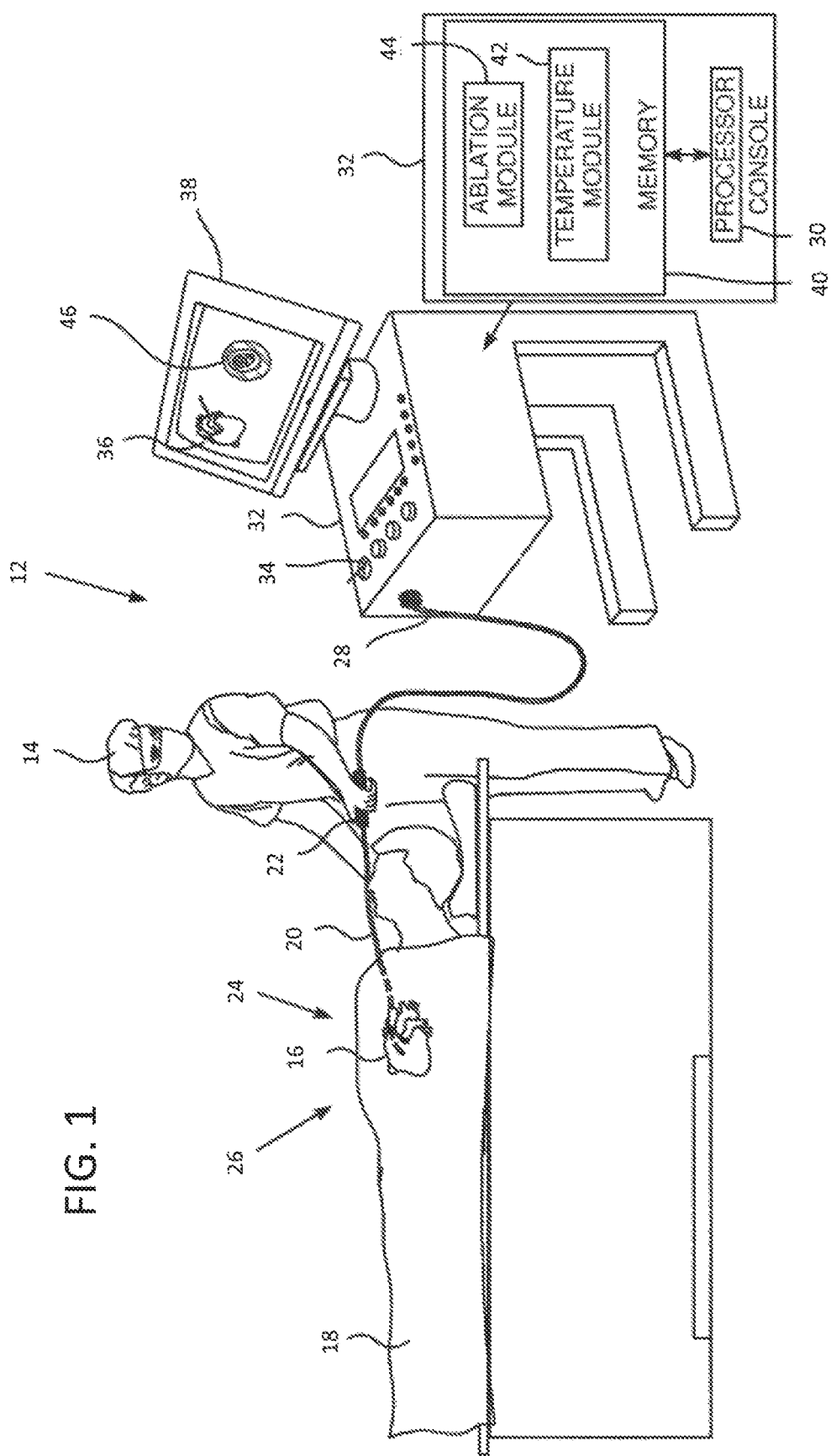
FIG. 1 is a schematic view of an ablation system in accordance with an embodiment of the present invention.

FIG. 1 is a schematic illustration of an invasive medical procedure using system 12, according to an embodiment of the present invention. The procedure is performed by a medical professional 14, and, by way of example, the procedure in the description hereinbelow is assumed to comprise ablation of a portion of a myocardium 16 of the heart of a human patient 18. However, it will be understood that embodiments of the present invention are not just applicable to this specific procedure, and may include substantially any procedure on biological tissue or on non-biological material.

In order to perform the ablation, professional 14 inserts a catheter 20 into a lumen of the patient, using handle 22, so that a distal end 24 of the catheter enters the heart of the patient. Distal end 24 comprises at least a tip electrode 26 for contacting locations of the myocardium. Catheter 20 has a proximal end 28 for connection to associated equipment as described below. Distal end 24 of the catheter is described in more detail with reference to FIGS. 3A, 3B and 3C.

System 12 is controlled by a system processor 30, which is located in an operating console 32 of the system. Console 32 comprises controls 34 which are used by professional 14 to communicate with the processor. During the procedure, processor 30 typically tracks a location and an orientation of distal end 24 of the catheter, using any method known in the art. For example, processor 30 may use a magnetic tracking method, wherein magnetic transmitters external to patient 18 generate signals in coils positioned in the distal end. The CARTO® system referenced above uses such a tracking method and additional details may be found in U.S. Pat. Nos. 5,391,199, 6,484,118, 6,239,724, 6,618,612, 6,332,089, 6,690,963, 7,729,742, in PCT Patent Publication WO 96/05768, and in U.S. Patent Publication No. 2004/0068178 A1, whose disclosures are all incorporated herein by reference.

The software for processor 30 may be downloaded to the processor in electronic form, over a network, for example. Alternatively or additionally, the software may be provided on non-transitory tangible media, such as optical, magnetic, or electronic storage media. The track of distal end 24 is typically displayed on a three-dimensional representation 36 of the heart 16 of patient 18 on a screen 38. In order to operate system 12, processor 30 communicates with a memory 40, which has a number of modules used by the processor to operate the apparatus. Thus, memory 40 comprises a temperature module 42 and an ablation module 44, for example, and typically comprises other modules, such as a force module for measuring the force on end 24, a tracking module for operating the tracking method used by processor 30, and an irrigation module allowing the processor to control irrigation provided for distal end 24. For simplicity, such other modules, which may comprise hardware as well as software elements, are not illustrated in FIG. 1. Processor 30 typically uses results of measurements of temperature acquired by module 42 to display on screen 38 a temperature distribution map 46.

Figure 2:
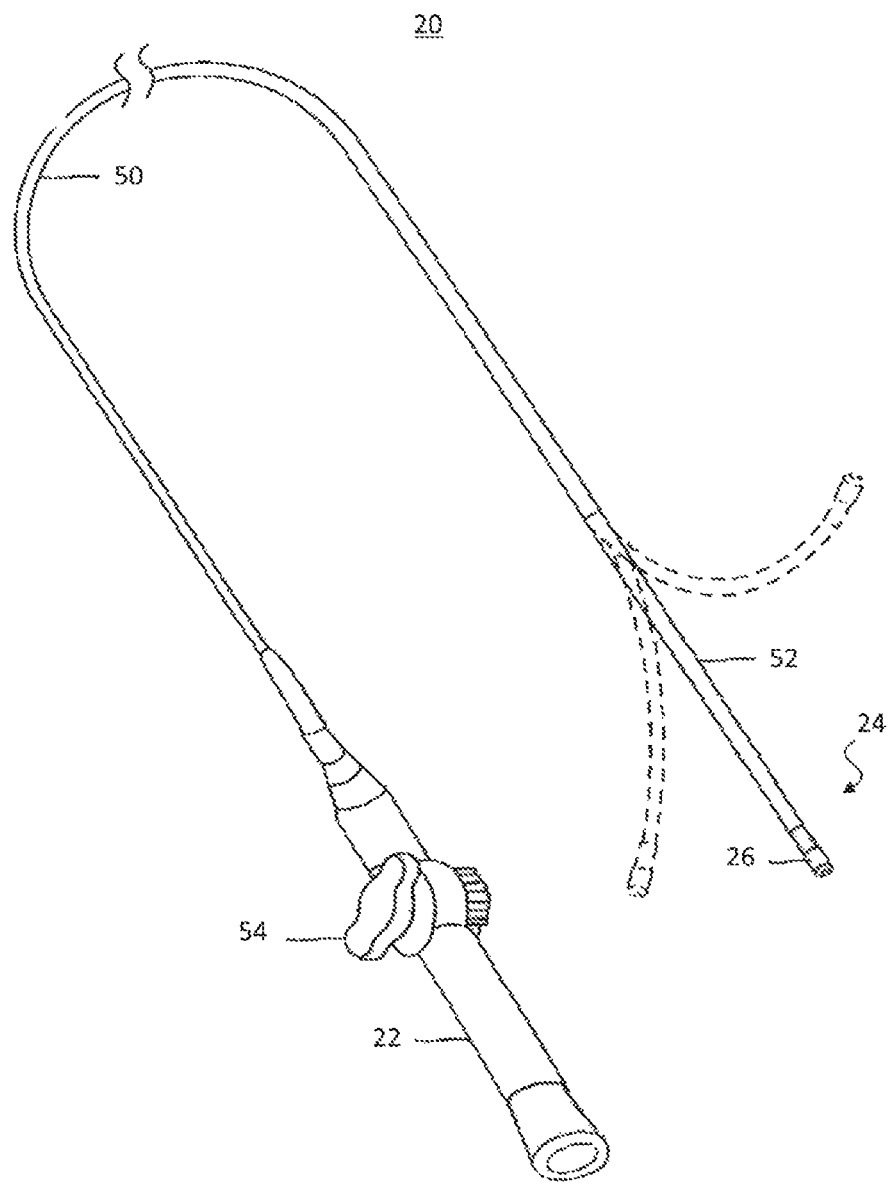
FIG. 2 is a perspective view of a catheter in accordance with an embodiment of the present invention.

A schematic elevational view of catheter 20 is illustrated in FIG. 2, showing an elongated body that includes an insertion shaft or catheter body 50 having a longitudinal axis, and an intermediate section 52 distal of the catheter body that optionally may be uni- or bi-directionally deflectable off-axis from the catheter body as indicated. Proximal of catheter body 50 is control handle 22 that allows an operator to maneuver the catheter as disclosed above, such as by deflecting intermediate section 52 when a steerable embodiment is employed. For example, control handle 22 may include deflection knob 54 that is pivoted in a clockwise or counterclockwise direction for deflection in the respective direction. In other embodiments, other steerable designs may be employed, such as the control handles for manipulating multiple control wires as described, for example, in U.S. Pat. Nos. 6,468,260, 6,500,167, 6,522,933 and 8,617,087, the entire disclosures of which are incorporated herein by reference.

Catheter body 50 is flexible, i.e., bendable, but substantially non-compressible along its length and may be of any suitable construction and made of any suitable material. In one aspect, an outer wall made of polyurethane or PEBAX may have an imbedded braided mesh of stainless steel or the like, as is generally known in the art, to increase torsional stiffness of catheter body 50 so that, when the control handle 22 is rotated, the intermediate section 52 will rotate in a corresponding manner Depending upon the intended use, the outer diameter of catheter body 50 may be approximately 8 french, and in some embodiments, may be 7 french. Likewise, the thickness of the outer wall of catheter body 50 may be thin enough so that a central lumen may accommodate any desired wires, cables and/or tubes, as will be described in further detail below. The useful length of the catheter, i.e., that portion that can be inserted into the body may vary as desired. In exemplary embodiments, the useful length may range from about 110 cm to about 120 cm. The length of the intermediate section 52 may correspond to a relatively small portion of the useful length, such as from about 3.5 cm to about 10 cm, and in some embodiments, from about 5 cm to about 6.5 cm.

Details regarding one embodiment of the distal end 24 of catheter 20 are illustrated in FIGS. 3A, 3B and 3C. As indicated, electrode 26 is configured as an elongated, generally cylindrical portion with an atraumatic distal portion. The shell of electrode 26 defines an interior cavity that is in fluid communication with a lumen extending the length of catheter body 50 to supply irrigation fluid. A plurality of irrigation apertures 54 are distributed substantially evenly across the surface of electrode 26, through which fluid may exit to outside of the electrode 26, to provide cooling of electrode 26 and the environment adjacent electrode 26 as desired. The shell of electrode 26 may be made of any suitable electrically-conductive material, such as palladium, platinum, gold, iridium and combinations and alloys thereof, including, Pd/Pt (e.g., 80% Palladium/20% Platinum) and Pt/Ir (e.g., 90% Platinum/10% Iridium).

In particular, FIG. 3A is a sectional view along the length of the probe, FIG. 3B is a cross-sectional view along a cut IIIB-IIIB that is marked in FIG. 3A, and FIG. 3C is a perspective view of a section of the distal end. As shown, electrode 26 is positioned distal to intermediate section 52 of the catheter body. Tip electrode 26 may have an approximately planar conducting surface 56 at its distal end and a substantially columnar surface 58 positioned proximally. As desired, additional electrodes, such as electrode 60, may be configured as a ring electrode and may be positioned on intermediate section 52. An electrical conductor 62 conveys radio-frequency (RF) electrical energy from ablation module 44 (FIG. 1), through catheter body 50, to electrode 26, and thus energizes the electrode to ablate myocardial tissue with which the electrode is in contact. Module 44 controls the level of RF power dissipated via electrode 26. During the ablation procedure, cooling fluid flowing out through apertures 54 may irrigate the tissue under treatment.

Temperature sensors 64, comprising thermocouples which are typically copper-constantan thermocouples, and also referred to herein as thermocouples 64, are mounted within tip electrode 26 at locations that are arrayed around the distal tip of the catheter, both axially and circumferentially. This example contains six sensors, with one group of three sensors in a distal location, close to the tip, and another group of three sensors in a slightly more proximal location. This distribution is shown only by way of example, however, and greater or smaller numbers of sensors may be mounted in any suitable locations within the tip electrode 26. Thermocouples 64 are connected by leads (not shown in these views) running through the length of catheter body 50 to provide temperature signals to temperature module 42.

In the disclosed embodiment, tip electrode 26 features a side wall 66 that is relatively thick, on the order of 0.5 mm thick, in order to provide the desired thermal insulation between temperature sensors 64 and the cooling fluid inside a central cavity 68 of the tip. The cooling fluid exits cavity 68 through apertures 54 as noted above. Again with respect to this embodiment only, sensors 64 are grouped as pairs of proximal and distal thermocouples within three separate thermocouple assemblies 70, which are fitted into longitudinal bores 72 in side wall 66. As described in further detail below, thermocouple assemblies 70 may be sized to fit closely with longitudinal bores 72, and may be held in place at their distal ends by a suitable cement 74, such as epoxy. The arrangement described above provides an array of six sensors 64, but other arrangements, and use of other numbers of sensors, may be employed as desired as will be apparent to those having ordinary skill in the art. All such arrangements and numbers are included within the scope of the present disclosure. Desirably, temperature sensors 64 may be positioned at different locations in proximity to the outer surfaces of electrode 26. Sensors 64 may be in proximity to and thermal communication with the outer surfaces, and may be thermally insulated from, rather than immersed in, the cooling irrigation fluid delivered from cavity 68 through apertures 54. The sensors thus provide multiple temperature readings that are substantially independent of the cooling fluid temperature, at different locations on tip electrode 26. The sensor that gives the highest temperature reading may be the one that is in contact with the tissue being ablated, and the temperature measured by this sensor varies linearly with the actual tissue temperature. Flow of the irrigation fluid may be generally lower in areas that are in firm contact with the tissue, and the sensors in these areas typically give the highest temperature readings. In some applications, the reading from the "hottest" sensor may thus be used in particular to monitor the tissue temperature and control the applied power and duration of the ablation procedure in order to obtain the desired therapeutic result without excessive tissue damage. Alternatively or additionally, the temperature readings of the multiple sensors can be combined and interpolated to give a map of temperature over the area of the catheter tip.

In the description herein, distal end 24 is assumed to define a set of xyz orthogonal axes, where an axis 76 of the distal end corresponds to the z axis of the set. For simplicity and by way of example, the y axis is assumed to be in the plane of the paper, the xy plane is herein assumed to correspond to the plane orthogonal to the z axis, and the origin of the xyz axes is assumed to be the center catheter body 50.

Typically, distal end 24 contains other functional components, which are outside the scope of the present disclosure and are therefore omitted for the sake of simplicity. For example, the distal end of the catheter may contain steering wires, as well as sensors of other types, such as a position sensor and a force sensor. Catheters containing components of these kinds are described, for example, in U.S. Pat. No. 8,437,832 and U.S. Patent Publication No. 2011/0130648, which are incorporated herein by reference.

Figure 4:
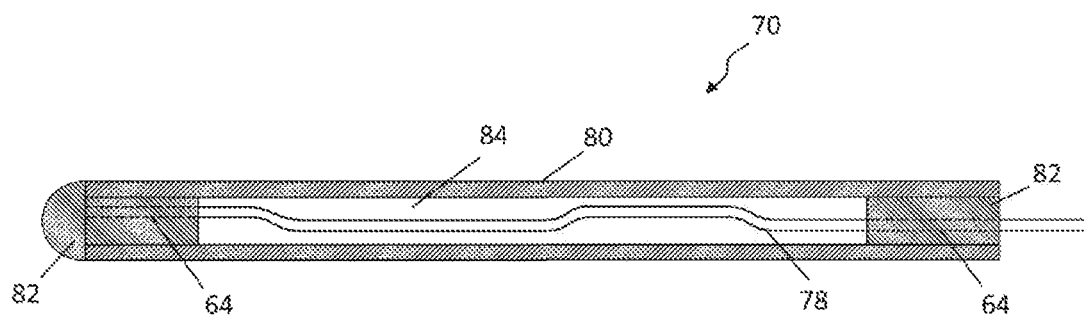
FIG. 4 is a cross sectional view of a thermally-isolated thermocouple in accordance with an embodiment of the present invention.

As discussed above, thermocouple assemblies 70 may be disposed within each longitudinal bore 72. Further details regarding thermocouple assembly 70 may be appreciated in reference to FIG. 4, which schematically shows proximal and distal sensors 64 formed by thermocouple junctions, both of which are coupled to leads 78 for communicating electrical signals to the proximal end of catheter 20. Sensors 64 are disposed within tubular element 80 and sealed at each end by thermally conductive material 82. Notably, the seals provided by thermally conductive material 82 create air gap 84 between sensors 64 to help isolate the sensors from each other and allow a more accurate measurement of the temperature adjacent each sensor. Each thermocouple junction forming sensor 64 may be accurately positioned at a desired location within tubular element 80 prior to being fixed in place by thermally conductive material 82. To help control the relative location of the thermocouple junctions within tubular element 80, leads 78 may be twisted about each other. For example, approximately 20-30 twists per inch may constrain sensors 64 relative to axis 76 (the z-axis as depicted in FIGS. 3A, 3B and 3C) and reduce the tendency for the thermocouple components to make contact with the inner diameter of tubular element 80 and conduct heat directly from the tube surface. Sensors 64 may be formed by a temperature measuring junction between a pair of leads 78. For example, any insulating covering on leads 78 may be stripped so that they may be soldered together to form the junction. Correspondingly, thermally conductive material 82 may be electrically insulating to protect the junction from shorting against electrode 26 or other component as well as providing the seal that, in conjunction with the inner diameter of tubular member 80, define air gap 84.

As discussed above, thermocouple assembly 70 is then secured, such as by cement 74 at a defined location within longitudinal bore 72. The close fit between tubular element 80 and longitudinal bore 72 may help ensure the thermocouple assembly is reproducibly positioned at its intended location by reducing any concentricity variation of the sensors 64 with respect to the tip shell longitudinal bores 72, allowing for more repeatable and predictable thermocouple response time/voltage output between catheters.

As will be appreciated, the techniques of this disclosure regarding thermocouple assembly 70 significantly increase thermal conductivity, allowing for greater temperature response. Moreover, tubular element 80 and thermally conductive material 82 effectively envelope the thermocouple components, helping to isolate them from tip electrode 26 and reduce the risk of shorting. Still further, thermocouple assembly 70 allows sensors 64 to be placed in the same relative position during manufacture, thereby improving temperature reproducibility and repeatability. As noted, air gap 84 helps distinguish measurements made by proximal and distal sensors 64 so that they function more independently. This characteristic may be more desirable depending on the intended application of catheter 20. For example, during parallel ablation the distal tip of electrode 26 may not be in contact with tissue, but the independently-functioning proximal sensor 26 may still measure the temperature response. Thus, thermocouple assembly 70 may increase the heat transfer rate from the outer tip shell of electrode 26 to the proximal and distal thermocouple junctions of sensors 64 while concurrently thermally isolating the sensors with air gap 84.

Thus, according to the techniques of this disclosure, thermocouple assembly 70 provides improved temperature response and accuracy, which are important characteristics in completing a successful procedure. Indeed, these techniques allow for accurate and consistent placement of the thermocouple junctions forming sensors 64 within thermocouple assembly 70, leading to repeatable and reproducible temperature response results. In comparison, conventional techniques do not provide for consistent placement of the sensors relative to the tip electrode, and such catheters suffer from a lack of consistency between units as a result. Moreover, the temperature response of the catheter may not be representative of the tissue temperature during ablation due to suboptimal thermal conductivity and the potential of incorrect placement of the thermocouple junctions within the tip shell. In particular, relatively larger clearances between the thermocouples and the bore or other recess of the electrode lead to a propensity for wide variation of sensor orientation with respect to the tip shell. Further, conventional designs that do not adequately isolate the proximal and distal thermocouple junctions exhibit a thermoelectric effect that is extended and continuous, being distributed along the entire length of the thermocouple conductors (corresponding to leads 78) between the junctions. Temperature differences, or gradients, through which these conductors pass influence and average the thermocouple readings when the sensors are inadequately thermally isolated. Conventional designs that utilize a thin polyimide covering are susceptible to deformation during manufacture, which again can result in variability of positioning of the sensors. This differences in positioning may also lead to different distributions of the volume that is filed with epoxy, again affecting reproducibility, as different thermal responses may be created.

Tubular element 80 may be formed from any suitable material that offers sufficient thermal conductivity while being electrically insulating. Suitable materials are also relatively impermeable, so that air gap 84 may be created by sealing the ends with thermally conductive material 82. Materials that are clear or semi-transparent for inspection of voids and bubbles of the thermally conductive material are also preferred. Exemplary materials include quartz, glass, alumina, polyimide and aluminum nitride ceramics. In one aspect, tubular element 80 may be see through or clear to aid in manufacturing assembly and defect inspection purposes. Tubular element 80 desirably allows for relatively tight tolerances in inner and outer diameter to reduce concentricity variation. Thermocouple assembly 70 desirably has a low thermal expansion coefficient so that during rapid tip shell heating, the buildup of internal stresses due to interference fitment with the tip shell are reduced. It is also desirable to configure thermocouple assembly 70 to withstand repeated thermal shocks during to RF ablation. Tubular element 80 may be designed with an appropriate outside diameter to fit with close tolerance inside longitudinal bore 72 as discussed. The diameter of tubular element 80 may therefore vary depending on the embodiment and the configuration of the tip electrode. Air gap 84 may be formed from ambient air captured by sealing the ends of tubular element 80. Air is a very effective thermal insulator with a thermal conductivity of 0.024 W/m*K. However, in other embodiments, other thermally and electrically isolating materials may be used as desired. Moreover, although thermocouple assembly 70 has been described in the context of having two sensors, proximally and distally located, it will be appreciated that other number of sensors may be employed. Each sensor may be sealed with thermally conductive material 82 to create air gaps 84 between them.

Thermally conductive material 82 as noted above may exhibit good heat transfer while being electrically insulating. For example, epoxy resins doped with thermally conductive fillers (40-80% fill by weight), such as silver nitrate and others as described below, may be utilized to provide a high heat transfer adhesive with heat transfer coefficients in the range of 3.5-10 W/m*K. Epoxies have desirable characteristics, including low temperature cure profile, good compliance, low outgassing and good thermal stability at elevated temperatures, while readily accepting fillers. The thermal conductivity of the epoxy is influenced by the type of filler, the percentage of filler loading, and size/shape of the filler particle; all of which may have a role in the overall viscosity/rheology of the epoxy formulation. Some exemplary filler materials that may be utilized to provide thermal conductivity and electrical isolation include, boron nitride-30 W/m*K, aluminum nitride-285 W/m*K and monocrystalline synthetic diamond 2000-3300 W/m*K. The incorporation of filler particles into an adhesive may increase thermal conductivity and lower the thermal expansion coefficient of the adhesive. Given that increasing filler loadings may result in a higher viscosity that is more difficult to fill small bore tubing due to capillary action of the adhesive, the relative benefits may be balanced and adjusted as warranted. In other embodiments, a UV curing adhesive may be also utilized to rapidly cure the adhesive even with filler particle ranges in the 50-70% (by weight) range, particularly due to the relative small volume of thermally conductive material 82 needed to seal the ends of tubular element 80 (for example, on the order of 0.0092-0.0139 $mm^3$.) Alternative UV adhesives such as acrylated urethanes with shadow or secondary heat cures may be also mixed with thermally conductive fillers to provide an acceptable heat transfer adhesive for thermally conductive material 82. Other suitable materials include epoxies, acrylic and silicone based adhesive formulations. In some embodiments, the longitudinal length of thermally conductive material 82 may be in the range of approximately 0.02" to 0.03" to provide good thermocouple response and conductor isolation.

To help illustrate certain aspects associated with the techniques of this disclosure, a representative embodiment of thermocouple assembly 70 may be compared to a conventional design. An example of an existing thermocouple assembly may have proximal and distal sensors encased in epoxy Loctite (P-9221), having a thermal conductivity of 0.19 W/m*K. The epoxy encased thermocouples are covered with polyimide having a thermal conductivity of 0.12 W/m*K. The resulting thermocouple design has an outer diameter (0.0071" inches-nominal, but typically is deformed to varying degrees during manufacture) and nests into a drilled hole in the platinum tip shell (0.0115" diameter nominal), creating approximately 0.0044" inches of radial clearance (nominal) between the tip shell hole and the polyimide tube outside diameter before the thermocouple assembly is adhesively bonded to the tip shell. As discussed above, this large clearance combined with distorted polyimide tube (due to handling) is potted with polyurethane adhesive that has a thermal conductivity of about 0.21 W/M*K. Variations in thermocouple response may occur as a result of the concentricity variation of the thermocouple with respect in the tip shell hole. For example, the 0.0071" diameter thermocouple package may abut the tip shell outer wall or may be up to 0.0044" away from the wall with 0.0044 inches of low thermally conductive polyurethane adhesive in between the thermocouple assembly and the tip shell wall.

For comparison, a thermocouple assembly 70 having the characteristics described above may be formed using a clear fused quartz tube (1.3 W/m*K) as tubular element, with an outside diameter 0.010"+/−0.001" and an inside diameter of 0.0059"+/−0.0006" and a 0.112"+/−0.002" length. Using the same tip shell configuration with a longitudinal bore 72 diameter of 0.0115" results in a nominal clearance of 0.0015 inches. In other embodiments, thermocouple assembly 70 and longitudinal bore 72 may have a nominal clearance range from 0.001-0.002 inches. Thermally conductive material 82, used to seal tubular element 80, may have a fill length of approximately 0.02" to 0.03" for this example, and may be formed from an epoxy potting compound 122-39 (SD) having a thermal conductivity of 3.5 W/m*K, available from Creative Materials (Ayer, Mass.). As noted above, air gap 84 has a thermal conductivity of 0.024 W/m*K.

Calculations regarding these examples demonstrate the conventional thermocouple assembly has 0.0993 W of heat transfer to the proximal and distal sensors as compared to the delivery of 0.803 W to proximal and distal sensors 64 of the thermocouple assembly 70 in this embodiment. As such, the heat transfer rate in Watts to the sensors is more than 8 times greater than the conventional thermocouple assembly. Further, air gap 84 provides effective thermal isolation between proximal and distal sensors 64. Given the heat transfer of 0.803 W to proximal and distal sensors 64 noted above, heat transfer to the middle of air gap 84 may be calculated to be approximately 0.018 W, resulting in more than 44 times less heat transfer to the center portion of the thermocouple assembly 70, isolating thermocouple leads 78 from the junctions and any thermal gradients that exist between the junctions.

Figure 5:
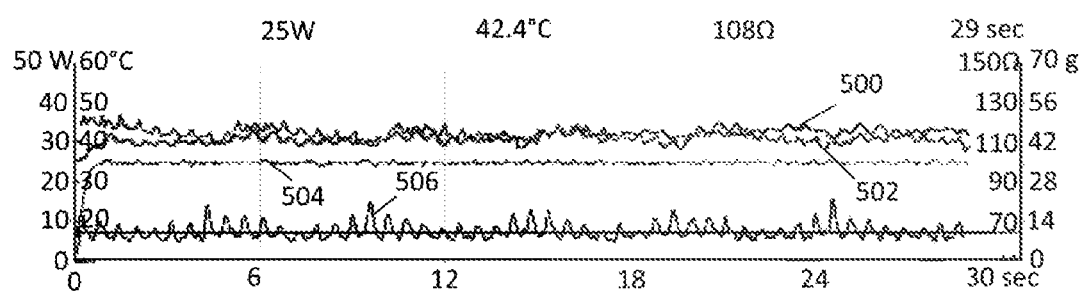
FIG. 5 graphically depicts results achieved with a conventional thermocouple.
Figure 6:
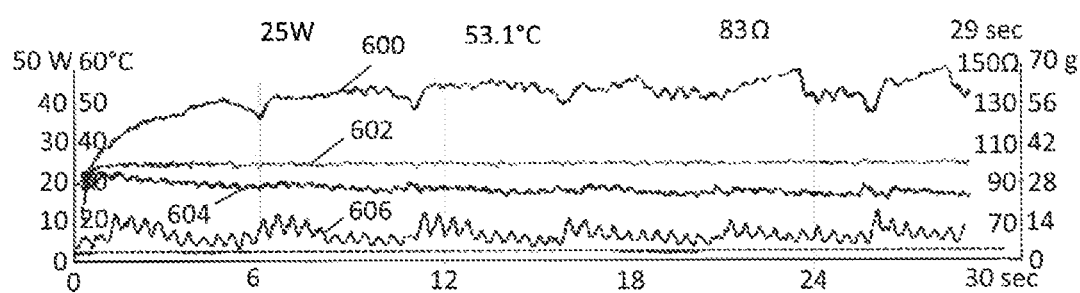
FIG. 6 graphically depicts results achieved with a thermally-isolated thermocouple for comparison to the conventional thermocouple in accordance with an embodiment of the present invention.

A comparison of the performance of the exemplary embodiment of thermocouple assembly 70 discussed above with the reference conventional assembly is depicted by FIGS. 5 and 6. In particular, FIG. 5 graphically illustrates the performance characteristics of the conventional thermocouple assembly, with trace 500 representing the measured temperature, trace 502 representing impedance, trace 504 representing power delivery and trace 506 representing the catheter tip electrode force in grams. Similarly, FIG. 6 graphically illustrates the performance characteristics of the test embodiment of thermocouple assembly 70, with trace 600 representing the measured temperature, trace 602 representing impedance, trace 604 representing power delivery and trace 606 representing the catheter tip electrode force in grams. As will be appreciated, the conventional design measured a maximum temperature of 45.4° C., with an average of 45.4° C. and an average impedance of 108Ω, as compared to the maximum temperature of 59.4° C., average temperature of 52.3° C. and average impedance of 108Ω over the course of a 29 sec procedure at a power level of 25 W. Correspondingly, the techniques of this disclosure may be seen to provide for the thermocouple assembly having the features of this disclosure greater temperature response. The tests depicted in FIGS. 5 and 6 were conducted in relative thin tissue, approximately 4 mm, and at the same irrigation flow rates of 8 ml/min, the thermocouple assembly embodying the techniques of this disclosure represents an increase in measured temperature in the range of approximately 7-10° C. For applications involving thicker tissue, a temperature increase of approximately 10-15° C. may be obtained at similar flow rates.

Described herein are certain exemplary embodiments. However, one skilled in the art that pertains to the present embodiments will understand that the principles of this disclosure can be extended easily with appropriate modifications to other applications.

What is claimed is:

1. A thermocouple assembly for use with an electrode, comprising:
    a plurality of temperature sensors formed by thermocouple junctions;
    an electrically insulating tubular element, wherein the plurality of temperature sensors are disposed within an inner diameter of the electrically insulating tubular element;
    a thermally conductive material sealing each of the plurality of temperature sensors within the tubular element; and
    a sealed air gap, defined by the thermally conductive material and the interior diameter of the tubular element between adjacent temperature sensors that thermally insulates each of the plurality of temperature sensors, the thermocouple assembly being disposed within a longitudinal bore, the bore contained completely within a sidewall of an electrode.

2. The thermocouple assembly of claim 1, wherein the tubular element comprises at least one of quartz, glass and polyimide.

3. The thermocouple assembly of claim 1, wherein the thermally conductive material comprises a UV curing adhesive.

4. The thermocouple assembly of claim 1, wherein the thermally conductive material has a thermal conductivity of at least 3.5 W/m*K.

5. The thermocouple assembly of claim 1, wherein leads connecting to the plurality of sensors are twisted to axially constrain the plurality of temperature sensors.

6. The thermocouple assembly of claim 1, wherein the thermocouple assembly and the longitudinal bore of the electrode have a nominal clearance of less than approximately 0.002 inches.

7. The thermocouple assembly of claim 1, wherein the thermally conductive material comprises an epoxy.

8. The thermocouple assembly of claim 7, wherein the epoxy comprises a filler that increases thermal conductivity in the range of approximately 40-80% by weight.

9. The thermocouple assembly of claim 1, wherein the plurality of temperature sensors comprise a proximal sensor and a distal sensor.

10. The thermocouple assembly of claim 9, further comprising at least one additional temperature sensor positioned between the proximal sensor and the distal sensor.

11. The thermocouple assembly of claim 9, wherein the thermally conductive material electrically insulates each of the plurality of temperature sensors.

12. A method for forming a thermocouple assembly, comprising:
    creating a plurality of temperature sensors with thermocouple junctions;
    disposing the plurality of temperature sensors within an inner diameter of an electrically insulating tubular element;
    sealing each of the plurality of temperature sensors within the electrically insulating tubular element with a thermally conductive material; and
    defining a sealed air gap between adjacent temperature sensors with the thermally conductive material and the interior diameter of the tubular element that thermally insulates each of the plurality of temperature sensors, the thermocouple assembly being disposed within a longitudinal bore, the bore contained completely within a sidewall of an electrode.

13. The method of claim 12, wherein sealing each of the plurality of the temperature sensors within the tubular element electrically insulates each of the plurality of temperature sensors.

14. The method of claim 12, further comprising twisting leads connecting to the plurality of temperature sensors to axially constrain the plurality of temperature sensors.

* * * * *